(12) United States Patent
Kitagawa et al.

(10) Patent No.: US 10,293,145 B2
(45) Date of Patent: May 21, 2019

(54) BALLOON CATHETER

(71) Applicant: PIOLAX MEDICAL DEVICES, INC., Yokohama-shi (JP)

(72) Inventors: Masanori Kitagawa, Yokohama (JP); Kazutaka Nanaumi, Yokohama (JP)

(73) Assignee: PIOLAZ MEDICAL DEVICES, INC., Yokohama-Shi, Kanagawa (JP)

( * ) Notice: Subject to any disclaimer, the term of this patent is extended or adjusted under 35 U.S.C. 154(b) by 231 days.

(21) Appl. No.: 15/515,068

(22) PCT Filed: Aug. 25, 2015

(86) PCT No.: PCT/JP2015/073880
§ 371 (c)(1),
(2) Date: Apr. 28, 2017

(87) PCT Pub. No.: WO2016/052009
PCT Pub. Date: Apr. 7, 2016

(65) Prior Publication Data
US 2017/0216567 A1    Aug. 3, 2017

(30) Foreign Application Priority Data
Sep. 30, 2014  (JP) ................................ 2014-201310

(51) Int. Cl.
*A61M 31/00*    (2006.01)
*A61M 37/00*    (2006.01)
(Continued)

(52) U.S. Cl.
CPC ........ *A61M 25/1006* (2013.01); *A61M 25/00* (2013.01); *A61M 25/0052* (2013.01);
(Continued)

(58) Field of Classification Search
CPC .. A61M 2025/0079; A61M 2025/1061; A61M 2025/1079; A61M 25/0052; A61M 25/10; A61M 25/1006
See application file for complete search history.

(56) References Cited

U.S. PATENT DOCUMENTS 4,909,258 A    3/1990  Kuntz et al.
4,932,959 A *  6/1990  Horzewski ............ A61M 25/01
                                                            604/96.01
(Continued)

FOREIGN PATENT DOCUMENTS

JP    H 01-145074 A    6/1989
JP    H 04-002363 A    1/1992
(Continued)

OTHER PUBLICATIONS

International Search Report (ISR) (PCT Form PCT/ISA/210), in PCT/JP2015/073880, dated Oct. 6, 2015.
(Continued)

*Primary Examiner* — Rebecca E Eisenberg
(74) *Attorney, Agent, or Firm* — McGinn IP Law Gropu, PLLC.

(57) ABSTRACT

One embodiment provides a balloon catheter which has an inner tube having a main lumen and an outer tube which forms an expansion lumen. A part of the inner tube is connected to the outer tube at a position closer to the proximal end than a balloon, a side hole is open at the connection section, and a weak section is provided to the inner tube a position closer to the distal end than the side hole. The weak section has lower rigidity than the remaining portion of the inner tube. When the balloon is expanded by fluid supplied to the expansion lumen, the weak section is pressed by the fluid pressure to thereby close the main lumen of the inner tube.

8 Claims, 8 Drawing Sheets

(51) Int. Cl.
*A61M 25/10* (2013.01)
*A61M 25/00* (2006.01)

(52) U.S. Cl.
CPC ..... *A61M 25/10* (2013.01); *A61M 2025/0018* (2013.01); *A61M 2025/0079* (2013.01); *A61M 2025/1061* (2013.01); *A61M 2025/1079* (2013.01)

(56) References Cited

U.S. PATENT DOCUMENTS

| | | | |
|---|---|---|---|
| 4,994,032 A | | 2/1991 | Sugiyama et al. |
| 5,176,637 A | | 1/1993 | Sagae |
| 5,217,482 A | * | 6/1993 | Keith ............... A61M 25/0662 604/102.02 |
| 5,360,403 A | | 11/1994 | Mische |
| 5,387,225 A | * | 2/1995 | Euteneuer ......... A61M 25/0029 604/913 |
| 5,573,508 A | | 11/1996 | Thornton |
| 6,045,531 A | | 4/2000 | Davis |
| 6,231,543 B1 | * | 5/2001 | Hegde .................. A61M 25/10 604/96.01 |
| 6,440,097 B1 | | 8/2002 | Kupiecki |
| 6,475,187 B1 | | 11/2002 | Gerberding |
| 6,540,721 B1 | * | 4/2003 | Voyles .................. A61B 17/22 604/103.1 |
| 6,706,010 B1 | | 3/2004 | Miki et al. |
| 2009/0247945 A1 | * | 10/2009 | Levit ................ A61M 25/1002 604/103 |
| 2011/0319923 A1 | * | 12/2011 | Watanabe ............. A61M 25/09 606/192 |
| 2012/0271232 A1 | * | 10/2012 | Katsurada ......... A61M 25/0052 604/103.09 |
| 2012/0302952 A1 | * | 11/2012 | Kitada ............. A61M 25/0021 604/96.01 |

FOREIGN PATENT DOCUMENTS

| | | |
|---|---|---|
| JP | H 08-215312 A | 8/1996 |
| JP | H 09-192231 A | 7/1997 |
| JP | H 10-509071 A | 9/1998 |
| JP | 2002-505166 A | 2/2002 |
| JP | 2002-119597 A | 4/2002 |
| JP | 2003-062082 A | 3/2003 |
| JP | 2004-533290 A | 11/2004 |
| JP | 2012-000390 A | 1/2012 |
| WO | WO 99/04845 A2 | 2/1999 |
| WO | WO 99/17831 A1 | 4/1999 |
| WO | WO 02/28465 A1 | 4/2002 |
| WO | WO 02/085443 A1 | 10/2002 |
| WO | WO 2012/110598 A1 | 8/2012 |

OTHER PUBLICATIONS

Written Opinion of International Preliminary Examining Authority (WO), dated Oct. 25, 2016, (IPRP-II) in PCT/JP2015/073880, and Partial English translation.
International Preliminary Examination Report with Regard to Patent Ability, dated Jan. 10, 2017, (IPRP-II) in PCT/JP2015/073880, and Partial English translation.

* cited by examiner

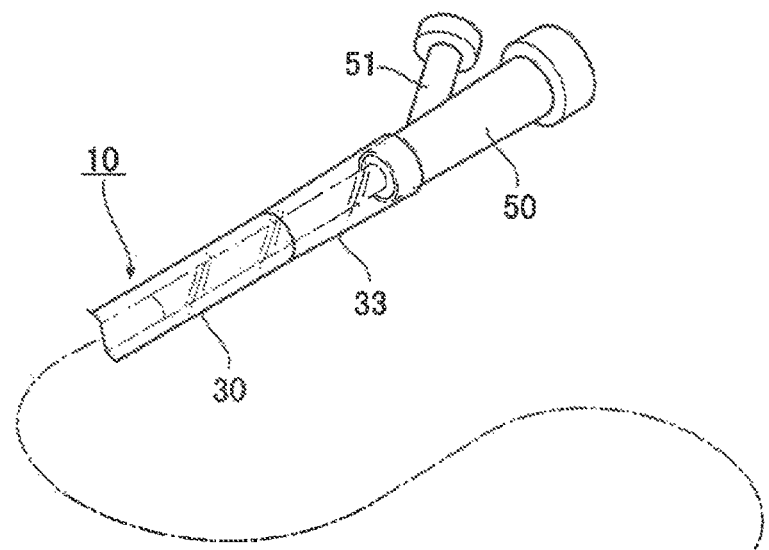
FIG. 1A
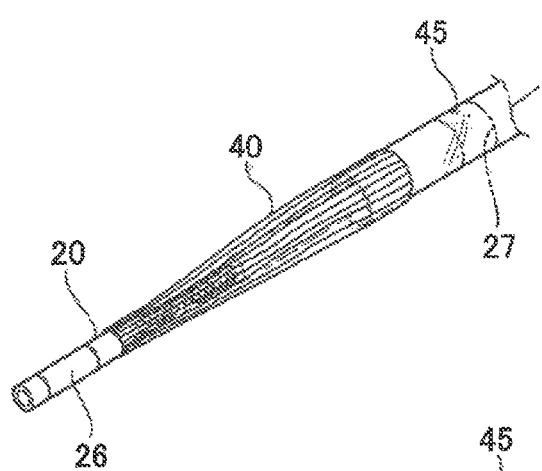
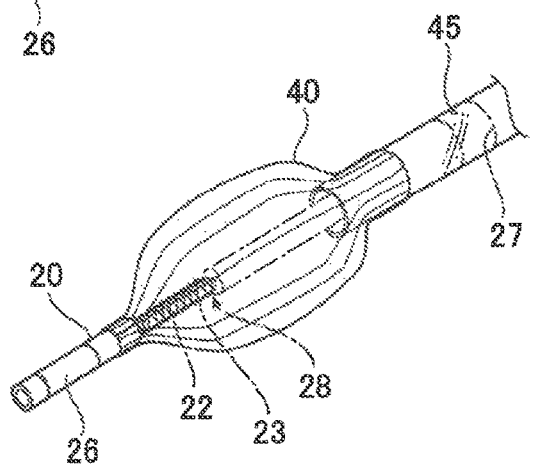
FIG. 1B

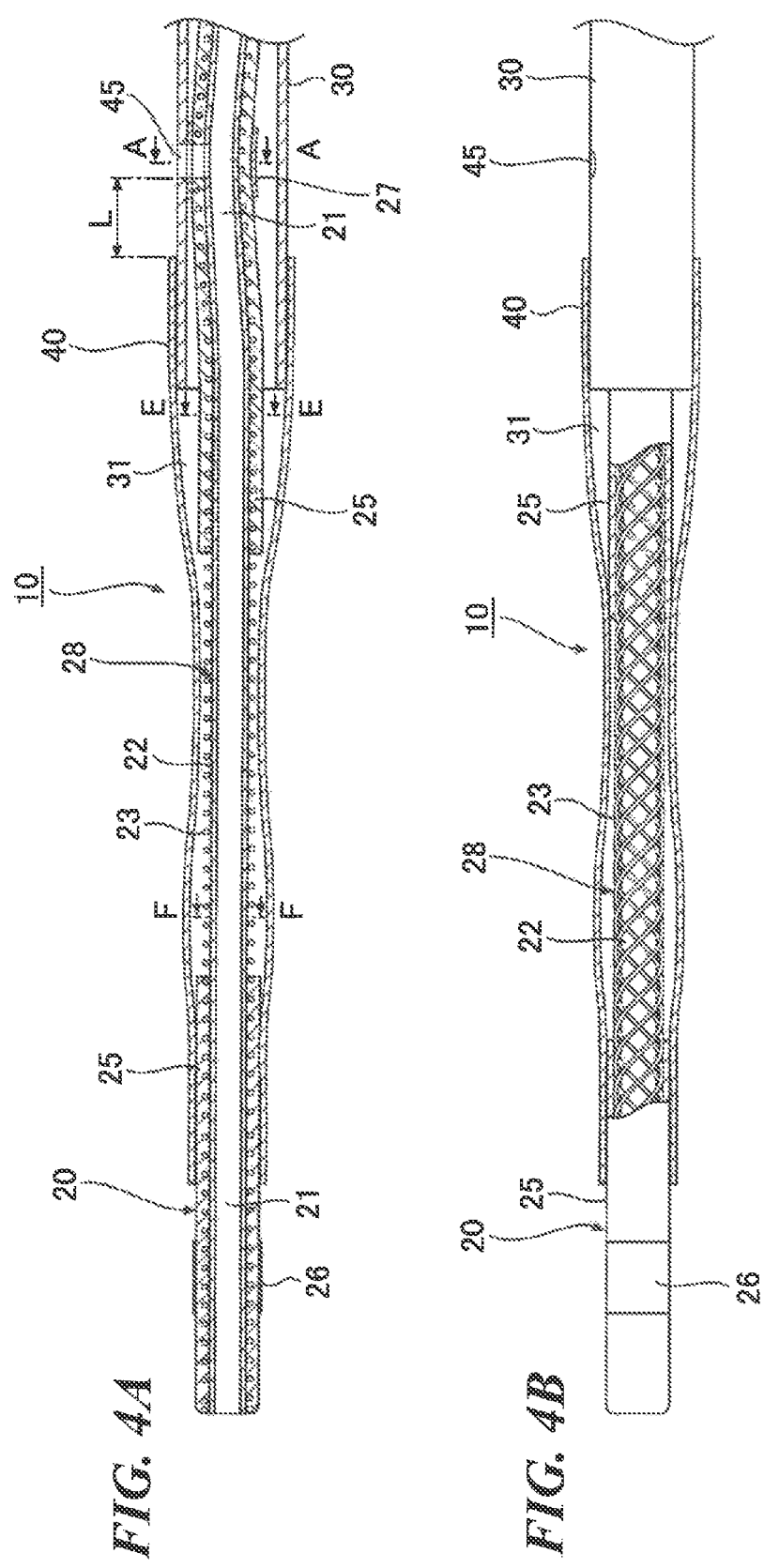

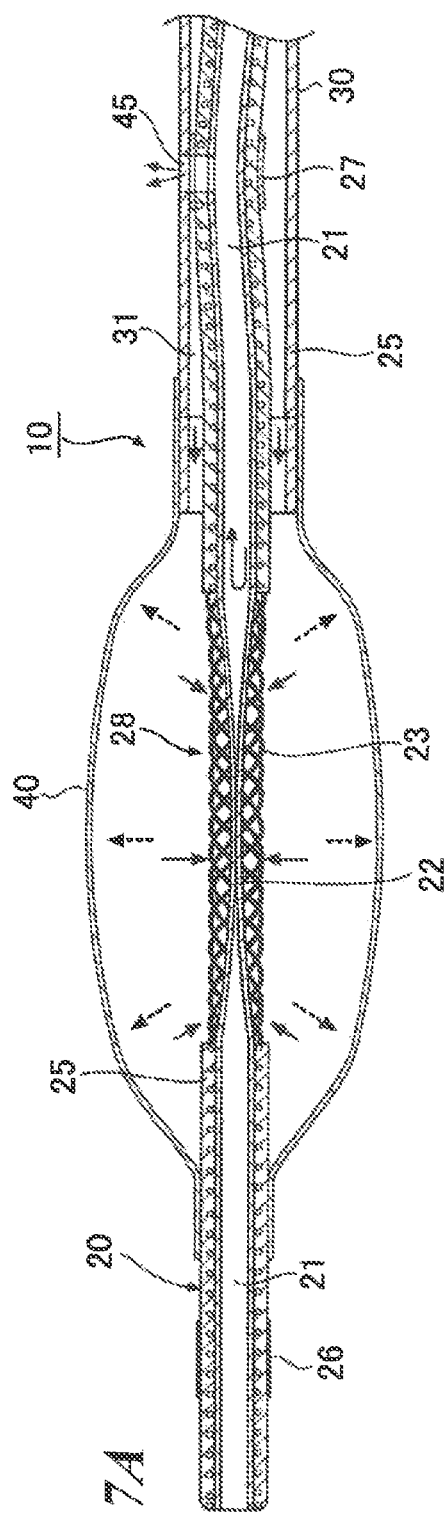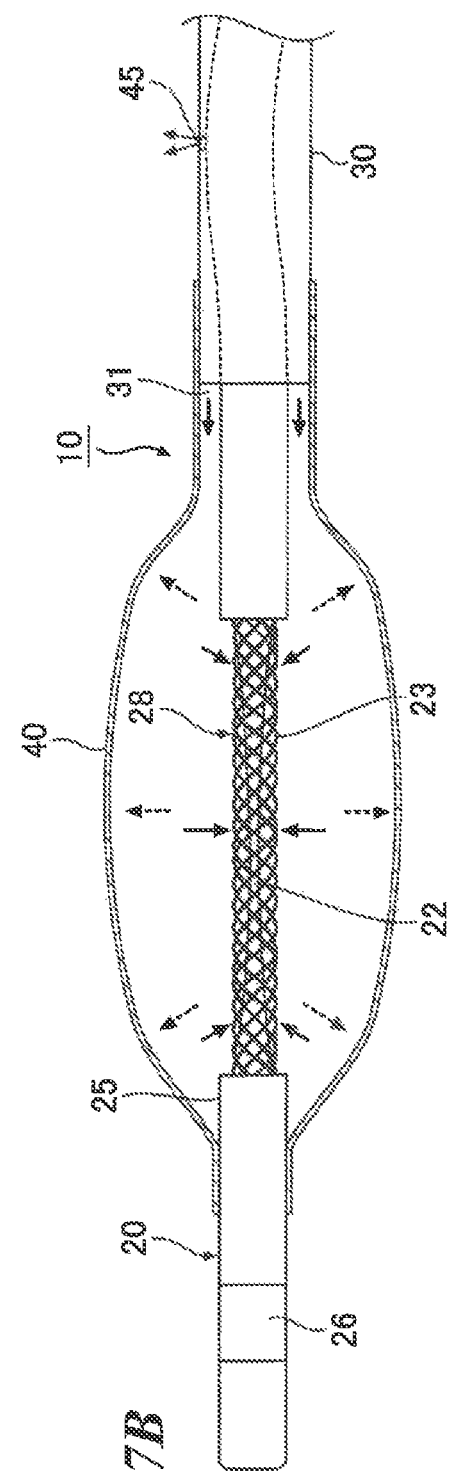

BALLOON CATHETER

TECHNICAL FIELD

The present invention relates to a balloon catheter through which, even in the case where a tubular organ branches into a main tube and a branch tube, a lesion part is in the branch tube, and the catheter cannot be introduced into the branch tube, for example, a medical solution or the like can be administered to the lesion part.

BACKGROUND ART

Conventionally, a tube-like catheter is inserted into a tubular organ such as the blood vessel, the ureter, the bile duct, or the trachea, and a contrast agent or a medical solution such as an anticancer agent or a nutrient is injected through the catheter. In the case where a lesion part such as cancer cells is produced in the liver, for example, a tip end portion of a catheter is indwelled in the hepatic artery which is in front of the lesion part, and a medical solution such as an anticancer agent is administered. In a tubular organ such as the hepatic artery, however, it is usual that the organ has a thick main tube, and a thin branch tube which branches off the main tube, and a case sometimes occurs where a catheter cannot be introduced into the thin branch tube.

In such a case, for example, a balloon catheter may be used which has: the tube-like body; an inflatable balloon which is placed on the outer circumference of a tip end portion of the body; and a side hole which is disposed on the side of the base end with respect to the place where the balloon is placed on the body. The balloon catheter is configured so that, by using a guide wire or the like, the tip end portion is placed in a portion of the main tube which is slightly beyond the portion where the branch tube branches off, the balloon is then inflated to close the main tube, a plug-like stopper is then inserted from the base end opening of the body to close the tip end opening of the body, a medical solution is injected from the base end side of the body in this state, to flow out from the side hole, and the medical solution is administered to the lesion part produced in the branch tube. In the case of such a balloon catheter, however, the plug-like stopper must be inserted into the body as described above, thereby closing the tip end opening of the body. Therefore, the work is cumbersome and troublesome, the surgical time is prolonged, and the burden on the patient is increased. Consequently, this countermeasure is not preferable.

Therefore, a balloon catheter which does not require a plug-like stopper has been proposed. For example, Patent Literature 1 below discloses an intravascular indwelling catheter having: a catheter body having a main inner cavity for injecting a medical solution, and a balloon inner cavity for inflating a balloon; a side hole which is formed in the middle of the catheter body, and which communicates with the main inner cavity; and a balloon portion which is placed in a tip end portion of the catheter body so as to communicate with the tip end opening of the balloon inner cavity. A physiological saline solution or the like is caused to flow into the balloon inner cavity to inflate the balloon portion in the tip end of the catheter body, and therefore the tip end opening of the main inner cavity is closed. When a medical solution is injected into the main inner cavity in this state the medical solution is allowed to flow out from the side hole, while preventing the the medical solution from flowing out from the tip end opening of the main inner cavity.

CITATION LIST

Patent Literature

Patent Literature 1: JP-A-2002-119597

SUMMARY OF INVENTION

Technical Problem

In the case of the intravascular indwelling catheter disclosed in Patent Literature 1, however, the balloon portion is placed in the tip end portion of the catheter body. Therefore, the outer diameter of the tip end side of the catheter is increased, and there is a possibility that the insertion characteristics of the catheter with respect to a tubular organ such as the blood vessel are lowered.

It is an object of the invention to provide a balloon catheter in which the diameter can be reduced, and the insertion characteristics of the catheter with respect to a tubular organ or the like can be improved.

Solution to Problem

To attain the object, the invention provides
a balloon catheter which has an inflatable balloon in a tip end portion, the balloon catheter including:
an inner tube which has a main lumen thereinside; and
an outer tube which is placed on an outer circumference of the inner tube, and which forms an inflation lumen with the inner tube to flow a fluid for inflating the balloon therethrough,
wherein a base end side of the balloon is fixed to the outer tube, whereas a tip end side of the balloon is fixed to the inner tube or the outer tube,
wherein a part of the inner tube is coupled to the outer tube at a side of a base end with respect to the balloon, and a side hole is formed in the coupling portion to cause the main lumen to be opened to an exterior,
wherein a weakened portion which is lower in rigidity than another portion of the inner tube is disposed on the inner tube at a side of a tip end with respect to the side hole, and
wherein the weakened portion is configured such that, when the balloon is inflated by the fluid supplied to the inflation lumen, the weakened portion is pressed by a pressure of the fluid to thereby close the main lumen of the inner tube.

There may be provided
the balloon catheter,
wherein the weakened portion is configured by forming a part of the inner tube to be thinner than another part.

There may be provided
the balloon catheter,
wherein the weakened portion of the inner tube includes:
an inner layer which is capable of closing the main lumen by being pressed by the fluid supplied to the inflation lumen; and
a reinforcing member which is placed on the outer circumference of the inner layer, and which is configured to allow the fluid to pass therethrough.

There may be provided
the balloon catheter,
wherein the inner tube includes:
the inner layer;
the reinforcing member; and
an outer layer which is placed on the outer circumference of the reinforcing member, and which clamps the reinforcing member with the inner layer, and
wherein, in the weakened portion, a part of the outer layer is peeled off to thereby expose the reinforcing member.

There may be provided
the balloon catheter,
wherein a base end side of the weakened portion is placed on a side of the tip end of the inner tube with respect to a place where the base end side of the balloon is fixed to the outer tube.

There may be provided
the balloon catheter,
wherein the weakened portion is formed in a whole circumference of the inner tube.

Advantageous Effects of Invention

According to the invention, when a fluid is supplied to the inflation lumen to inflate the balloon, the weakened portion disposed in the inner tube is pressed by the pressure of the fluid, and the main lumen of the inner tube is closed. When a fluid such as a medical solution is injected into the main lumen of the inner tube, therefore, the fluid is allowed to flow out through only the side hole to the exterior while not being allowed to flow out from the tip end opening of the main lumen. Accordingly, the diameter of the balloon catheter can be reduced, and the insertion characteristics of the catheter with respect to a tubular organ, a body cavity, and the like can be improved.

BRIEF DESCRIPTION OF DRAWINGS

FIGS. 1A and 1B show an embodiment of the balloon catheter of the invention. FIG. 1A is a perspective view of the balloon catheter. FIG. 1B is an enlarged perspective view of a state where a balloon is inflated.

FIGS. 4A and 4B show a state where, in the balloon catheter, the balloon is not inflated. FIG. 4A is an enlarged sectional view of main portions. FIG. 4B is a partially cutaway enlarged side view of main portions.

FIGS. 7A and 7B show a state where, in the balloon catheter, the balloon is inflated. FIG. 7A is an enlarged sectional view of main portions. FIG. 7B is a partially cutaway enlarged side view of main portions.

DESCRIPTION OF EMBODIMENTS

Hereinafter, an embodiment of the balloon catheter of the invention will be described with reference to the drawings.

As shown in FIGS. 1 to 4B, the balloon catheter 10 has an inflatable balloon 40 in a tip end portion, and has an inner tube 20, and an outer tube 30 which is placed on the outer circumference of the inner tube.

Figure 2:
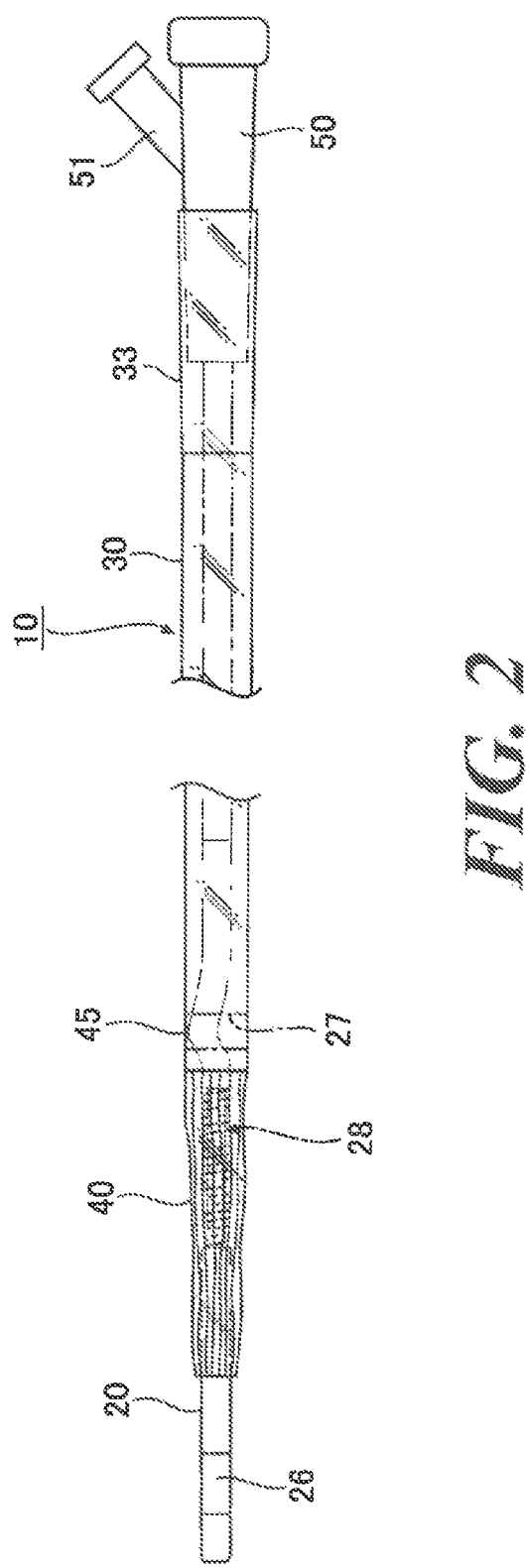
FIG. 2 is a side view of the balloon catheter.
Figure 3:
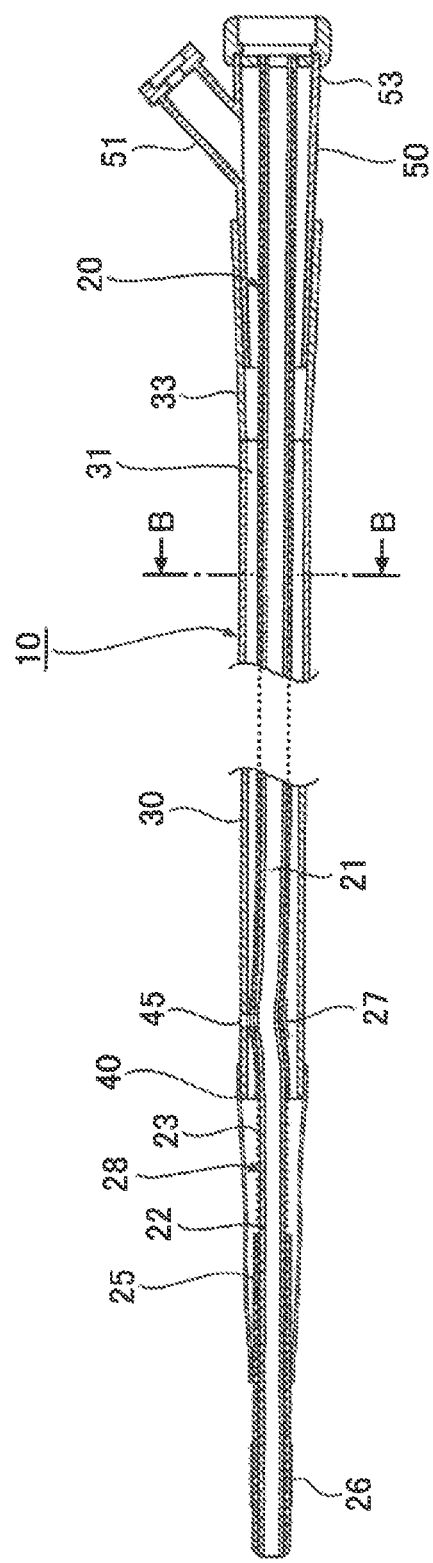
FIG. 3 is a sectional view of the balloon catheter.
Figure 5A:
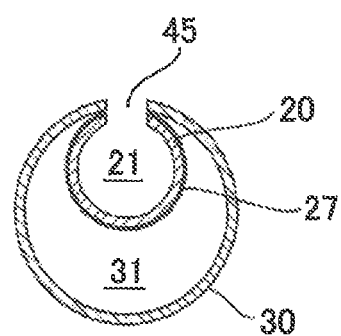
FIG. 5A is a sectional view taken along arrow lines A-A in FIG. 4A.
Figure 5B:
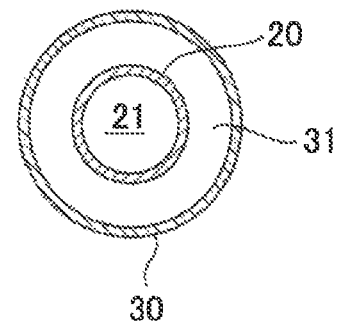
FIG. 5B is a sectional view taken along arrow lines B-B in FIG. 3.

As shown in FIGS. 3 and 5B, the inner tube 20 includes a main lumen 21 thereinside. A guide wire that is not shown, and a fluid such as an anticancer agent, a nutrient, or another medical solution are to be injected.

As shown in FIG. 3, by contrast, the outer tube 30 is placed coaxially with the inner tube 20 to form a double tube structure. An inflation lumen 31 through which a fluid for inflating the balloon 40 is to flow is formed between the outer circumference of the inner tube 20 and the inner circumference of the outer tube 30 (see FIG. 5B).

In FIGS. 5A and 5B, for the sake of the drawings, the inner tube 20 is shown while omitting an inner layer 22 and outer layer 25 which will be described later.

The outer tube 30 has a shape in which the diameter of a base end portion 33 is slightly increased. The base end portion 33 is press-fitted to the outer circumference of a tip end portion of a hub 50 which has a substantially tubular shape, whereby the hub 50 is coupled to the base end side of the outer tube 30.

The outer tube 30 is formed by, for example, polyethylene (PE), a fluorine resin, polyoxymethylene (POM), polypropylene (PP), a nylon resin, a polyester resin, an ABS resin, a polycarbonate resin, polyetheretherketone (PEEK), a polyimide resin, or polyurethane (PU). The outer tube 30 in the embodiment is formed by a resin with high transparency so that the inner side is visible (see FIGS. 1A, 1B and 2).

Alternatively, the outer tube 30 may be formed into one tube by coupling end portions of plural tubular members having different hardnesses. In this case, preferably, a tubular member having a higher hardness is placed in the base end side of the tube, and other tubular members in which the hardnesses are gradually lowered as further advancing toward the tip end of the tube are placed. The coupling structure between the outer tube 30 and the hub 50 is not limited to the above-described structure.

The hub 50 has a tubular fluid injection port 51 which elongates in an oblique outer direction toward the base end side of the hub, in a predetermined place of the outer circumference. The fluid injection port 51 communicates with the inflation lumen 31 (see FIG. 3).

As shown in FIG. 3, a tube fixation wall portion 53 in which a fitting hole is disposed in the middle is disposed in the inner cavity on the side of the base end of the hub 50. When the base end side of the inner tube 20 is fitted into the fitting hole of the tube fixation wall portion 53, the hub 50 is coupled to the base end side of the inner tube 20. The coupling structure between the inner tube 20 and the hub 50 is not limited to the above-described structure.

As shown in FIGS. 3, 4A and 4B, the balloon 40 covers the outer circumference of a tip end portion of the outer tube 30, the base end side of the balloon is fixed to the outer tube 30, the tip end side is fixed to the inner tube 20, the peripheral edges are sealed, and the inner cavity communicates with the inflation lumen 31. When a fluid such as a contrast agent or a physiological saline solution is injected from the fluid injection port 51 of the hub 50, therefore, the fluid flows through the inflation lumen 31 and enters the inner cavity of the balloon 40, and the balloon 40 is inflated by the pressure of the fluid (see FIGS. 7A and 7B). Alternatively, the the balloon 40 may be placed, for example, on the side of the inner circumference of the tip end portion of the outer tube 30. The placement portion of the balloon is not particularly limited.

The balloon 40 is formed by, for example, polyurethane, a nylon resin, or silicone. Although, in the balloon 40 in the embodiment, the tip end side is fixed to the inner tube 20, the tip end side may be fixed to the outer tube 30.

Figure 6A:
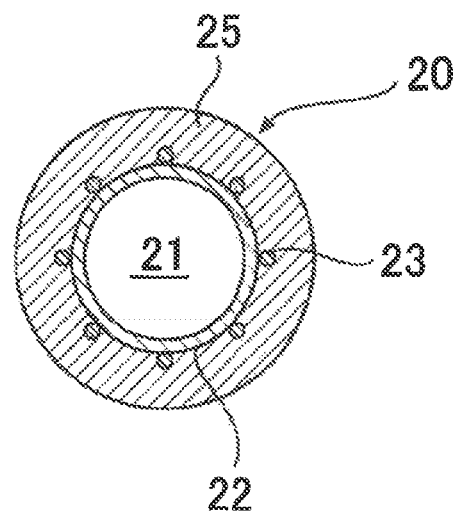
FIG. 6A is a sectional view taken along arrow lines E-E in FIG. 4A.

Returning to the description of the inner tube 20, as shown in FIGS. 4A, 4B, and 6A, the inner tube 20 in the embodiment is configured by: the inner layer 22 in which the main lumen 21 is disposed on the inner side; a reinforcing member 23 which is placed on the outer circumference of the inner layer 22; and the outer layer 25 which is placed outside the reinforcing member 23, and which clamps the reinforcing member 23 between the outer layer and the inner layer 22.

The inner layer 22 is preferably formed by, for example, a fluorine resin such as polytetrafluoroethylene (PTFE), tetrafluoroethylene, or perfluoroalkylvinylether copolymer (PFA), polyethylene (PE), polyoxymethylene (POM), polypropylene (PP), a nylon resin, a polyester resin, or polyimide (PI). Particularly preferably, the inner layer is formed by a fluorine resin such as polytetrafluoroethylene (PTFE), tetrafluoroethylene, or perfluoroalkylvinylether copolymer (PFA).

The outer layer 25 is preferably formed by, for example, polyurethane (PU), polyethylene (PE), polypropylene (PP), a nylon resin, or silicone. Particularly preferably, the outer layer is formed by polyurethane.

Preferably, the thickness of the inner layer 22 is 5 to 30 μm, and more preferably 10 to 15 μm. By contrast, the thickness of the outer layer 25 is 20 to 300 μm, and more preferably 80 to 120 μm.

As shown in FIG. 4B, the reinforcing member 23 in the embodiment has a coil-like shape that is formed by spirally winding a wire member in the axial direction of the inner tube 20, and has gaps which allow the fluid to pass therethrough. The reinforcing member 23 is placed on the outer circumference of the inner layer 22 without being fixed thereto, and can be separated from the outer circumference of the inner layer 22 when the diameter of the inner layer 22 is reduced (see FIG. 7B).

The reinforcing member 23 is not limited to have the above-describe coil-like shape, and may be formed into, for example, a braided member which is formed by knitting and/or braiding a wire member, a tubular member in which a slit is disposed in the axial or circumferential direction, or a tubular member in which incisions are formed so as to form a reed-like shape. The reinforcing member may have any shape as far as the member can reinforce the inner layer 22 and the fluid can pass through the member.

The reinforcing member 23 is formed by, for example, a metal wire member configured by a metal such as W, Au-plated W, stainless steel, or a Ni—Ti alloy, or a polyamide resin such as Nylon 6 or Nylon 66, a polyester resin such as polyethylene terephthalate (PET) or polybutylene terephthalate (PBT), or a like synthetic resin.

In the inner tube 20, as shown in FIGS. 2 to 4B, X-ray opaque annular markers 26, 27 are placed at a position which is separated by a predetermined distance from the tip end of the balloon, and that which is separated by a predetermined distance from the base end of the balloon, respectively. The markers 26, 27 are formed by, for example, Pt, Ti, Pd, Rh, Au, W, Ag, Bi, Ta, alloys of these metals, a synthetic resin containing powder of $BaSO_4$, Bi, W, or the like, or stainless steel.

In the inner tube 20, moreover, a part on the side of the base end with respect to the balloon 40, here, the portion where the marker 27 is placed is made close to a predetermined place of the inner circumference of the outer tube 20 as shown in FIGS. 3 and 4A, and then fixed together with the marker 27 to the inner circumference of the outer tube 30 by thermal welding, an adhesive agent which is not shown, or the like, whereby the part of the inner tube 20 is coupled to the outer tube 30. A side hole 45 which allows the main lumen 21 disposed in the inner tube 20 to be opened to the exterior is disposed in the coupling portion (see FIGS. 4A and 5A). The side hole 45 is configured so as to communicate with the main lumen 21 of the inner tube 20, and not to communicate with the inflation lumen 31 (see FIGS. 4A and 5A).

As shown in FIG. 4A, the distance L from the position where the base end side of the balloon 40 and the inner tube 20 are fixed to each other, to the side hole 45 is preferably 10 mm or shorter, and more preferably 5 mm or shorter.

In the embodiment, the portion of the inner tube 20 where the marker 27 is placed is coupled together with the marker 27 to the outer tube 30, and the side hole 45 is disposed in the coupling portion. Alternatively, a portion of the inner tube 20 where the marker 27 is not placed may be coupled to the outer tube 30, and the side hole 45 may be disposed. The side hole 45 is requested to be at least on the side of the base end with respect to the balloon 40.

Although, in the embodiment, the inner tube 20 is configured by one tube, the one tube may be configured by coupling end portions of plural tubular members having different hardnesses. In this case, preferably, a tubular member having a higher hardness is placed in the base end side of the tube, and other tubular members in which the hardnesses are gradually lowered as further advancing toward the tip end of the tube are placed.

In the balloon catheter 10, a weakened portion 28 which is in the inner tube 20, and which is lower in rigidity than the other portion of the inner tube 20 is disposed on the side of the tip end with respect to the side hole 45.

The weakened portion 28 in the embodiment is structured in the following manner. As described above, the inner tube 20 is configured by the inner layer 22, the reinforcing member 23, and the outer layer 25. By contrast, the weakened portion 28 in the embodiment has a structure which is configured by the inner layer 22 and the reinforcing member 23 that is placed on the outer circumference of the inner layer, and in which the outer circumference of the reinforcing member 23 is not covered by the outer layer 25, and a part of the inner tube 20 is formed to be thinner than the other part (see FIGS. 4A, 4B and 6B).

Figure 6B:
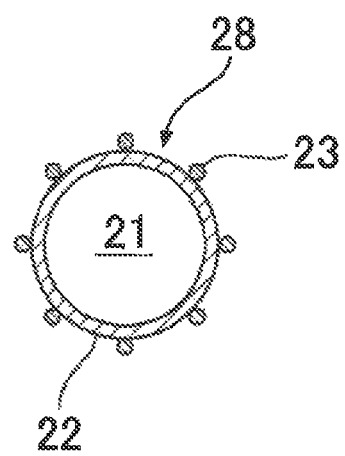
FIG. 6B is a sectional view taken along arrow lines F-F in FIG. 4A.

As shown in FIG. 6B, the weakened portion 28 is formed in the whole circumference of the inner tube 20.

In the embodiment, as shown in FIGS. 4A and 4B, a part of the outer layer 25, here, the portion where the balloon 40 is placed is peeled off, and the reinforcing member 23 is exposed, whereby the weakened portion 28 is disposed.

According to the embodiment, as described above, the weakened portion 28 can be formed simply by peeling off a part of the outer layer 25, and therefore the productivity of the balloon catheter 10 can be enhanced. Moreover, the inner tube 20 is configured by the inner layer 22, the reinforcing member 23, and the outer layer 25, and the reinforcing member 23 is clamped between the inner layer 22 and the outer layer 25. Therefore, positional displacement of the reinforcing member 23 can be suppressed.

As the means for exposing the reinforcing member 23, for example, a predetermined range of the outer layer 25 may be melted by an agent or cut away by a cutter; the outer layer 25 may be formed by a resin with a melting point which is lower than that of the inner layer 22, and a predetermined range of the outer layer 25 may be melted by heat; or the inner layer 22 and the reinforcing member 23 are covered by a pair of outer layers 25, 25 while forming a gap corresponding to the length of the weakened portion 28. The means is not particularly limited.

The weakened portion 28 in the embodiment is formed by the configuration in which a part of the inner tube 20 is formed to be thinner than the other portion by peeling a part of the outer layer 25. The weakened portion is requested to be lower in rigidity than the other portion of the inner tube, and the structure of the weakened portion is not particularly limited. Although the weakened portion 28 is formed in the whole circumference of the inner tube 20, the weakened portion may be disposed only in a predetermined range in the circumferential direction.

As shown in FIGS. 4A and 4B, moreover, the base end side of the weakened portion 28 is placed on the side of the tip end of the inner tube 20 with respect to the place where the base end side of the balloon 40 is fixed to the outer tube 30.

The weakened portion 28 is configured so that, when the balloon 40 is inflated by a fluid supplied to the inflation lumen 31, the weakened portion is pressed by the pressure of the fluid to close the main lumen 21 of the inner tube 20 (see FIGS. 7A and 7B).

In the embodiment, when a fluid is supplied into the inflation lumen 31, and the balloon 40 is inflated, the fluid passes through the gaps of the reinforcing member 23, and presses the inner layer 22 to reduce the diameter, thereby closing the main lumen 21 which is inside the inner layer 22 (see FIG. 7A). At this time, the reinforcing member 23 is placed on the outer circumference of the inner layer 22 without being fixed thereto, and, when the inner layer 22 is pressed and the diameter is reduced, the reinforcing member is therefore separated from the outer circumference of the inner layer 22 (see FIG. 7B).

Next, an example of a method of using the balloon catheter 10 having the above-described structure will be described.

The balloon catheter 10 can be used, for example, in the case where, in a bifurcation of a tubular organ, i.e., a portion having a thick main tube, and a thin branch tube which branches off the main tube, a catheter cannot be introduced into the branch tube.

Figure 8:
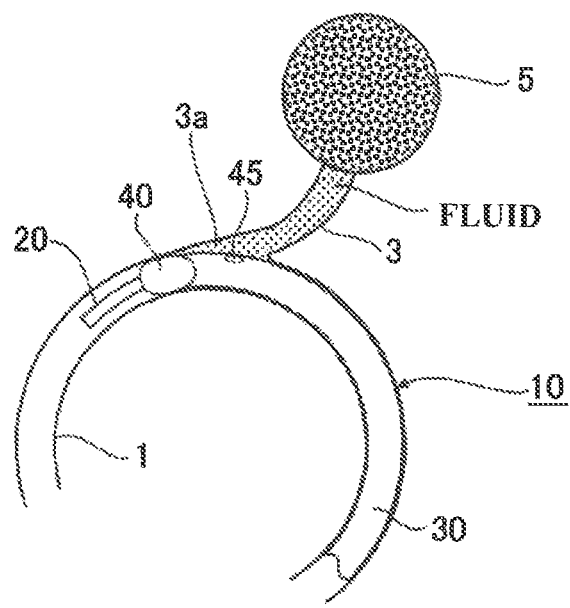
FIG. 8 is a view showing a state where the balloon catheter is used.

As shown in FIG. 8, the hepatic artery which is one of tubular organs has a a thick main tube 1, and a thin branch tube 3 which branches off and extends from the middle of the main tube 1 through a bifurcation 3a. A method of using the balloon catheter 10 in the case where a lesion part 5 such as liver cancer is produced on the tip end side of the branch tube 3, and a fluid such as an anticancer agent is to be injected to the lesion part 5 will be described. The balloon catheter 10 may be used also in, for example, a tubular organ such as the bile duct, the pancreatic duct, the ureter, or the trachea, and other body cavities of the human body. The use of the balloon catheter is not limited to the above-described use mode.

Firstly, a guide wire which is not shown is inserted into the main tube 1 by the well-known Seldinger technique or the like, and a tip end portion is caused to reach a position which is slightly beyond the bifurcation 3a. In this state, the guide wire is inserted into the main lumen 21 of the balloon catheter 10, and the balloon catheter 10 is moved by using the guide wire. Then, a tip end portion of the balloon catheter 10 is caused to reach a position which is slightly beyond the bifurcation 3a, and indwelled so that the side hole 45 is at a position matching the bifurcation 3a.

Then, the guide wire is pulled out from the interior of the main lumen 21 while holding and fixing the position of the balloon catheter 10, and thereafter a fluid such as a contrast agent is supplied from the fluid injection port 51 of the hub 50. As shown in FIGS. 7A and 7B, then, the fluid passes through the inflation lumen 31 to flow into the inner cavity of the balloon 40, thereby inflating the balloon 40. This causes the balloon 40 to butt against the wall surface of the main tube 1 to close the inner cavity of the main tube 1 (see FIG. 8). In conjunction with the inflation of the balloon 40 due to the fluid, the fluid passes through the gaps of the reinforcing member 23 constituting the weakened portion 28, and the pressure of the fluid presses the inner layer 22 constituting the weakened portion 28 to reduce the diameter, whereby the main lumen 21 which is inside the inner layer 22 is closed.

Next, a fluid such as an anticancer agent is supplied into the main lumen 21 from the base end side of the hub 50. Then, the fluid flows in the main lumen 21. At this time, the tip end portion of the main lumen 21 has been closed as described above, and therefore the fluid can be caused to flow out to the exterior from only the side hole 45, without allowing the fluid to flow out from the tip end opening of the main lumen 21.

As described above, the fluid flows out to the exterior from only the side hole 45, and then flows into the branch tube 3 through the bifurcation 3a. Therefore, the fluid such as an anticancer agent is blocked from flowing to the main tube 1 in which the lesion part 5 does not exist, and can be effectively administered to only the lesion part 5.

In the balloon catheter 10, as described above, the weakened portion 28 is disposed in the inner tube 20, and, when the balloon is inflated, the weakened portion is pressed by the pressure of a fluid to close the main lumen 21 of the inner tube 20. Unlike the intravascular indwelling catheter disclosed in Patent Literature 1, therefore, it is not necessary to place a balloon portion for closing the main inner cavity, in the tip end of the catheter body, the diameter of the balloon catheter 10 can be reduced, and the insertion characteristics of the catheter with respect to a tubular organ, body cavity, and the like can be improved.

In the balloon catheter 10, unlike a conventional balloon catheter, moreover, it is not necessary to insert a plug-like stopper into the body to close the tip end opening. As described above, the inflation of the balloon 40 which is due to the supply of a fluid into the inflation lumen 31 causes the weakened portion 28 to be pressed by the fluid pressure, and the main lumen 21 can be closed. Therefore, the work of administering an anticancer agent or the like by using the balloon catheter 10 can be performed easily and smoothly, the surgical time can be shortened, and the burden on the patient can be reduced.

In the embodiment, the weakened portion 28 is formed by thinning a part of the inner tube 20 as compared to the other part, and therefore the weakened portion 28 can be formed integrally with the inner tube 20. As a result, the productivity of the balloon catheter 10 can be enhanced, and the responsiveness in the case where the weakened portion 28 is pressed by the balloon inflation can be enhanced, so that the main lumen 21 of the inner tube 20 can be smoothly closed.

In the embodiment, furthermore, the weakened portion 28 of the inner tube 20 has the inner layer 22 which is pressed by a fluid supplied to the inflation lumen to be able to close the main lumen 21, and the reinforcing member 23 which is placed on the outer circumference of the inner layer 22, and which allows the fluid to pass therethrough. Therefore, the reduction of the rigidity in the weakened portion 28 can be suppressed by the reinforcing member 23, and the operability of the balloon catheter 10 can be maintained while ensuring the pushability, the torque transmission characteristics, and the like.

In the embodiment, as shown in FIG. 4A, the base end side of the weakened portion 28 is placed on the side of the tip end of the inner tube 20 with respect to the place where the base end side of the balloon 40 is fixed to the outer tube 30. Therefore, the side hole 45 can be disposed close to the base end side of the balloon 40 (when the base end side of the weakened portion 28 is on the side of the base end of the inner tube with respect to the fixation place of the base end side of the balloon 40, the distance between the base end side of the balloon 40 and the side hole 45 is increased). As shown in FIG. 8, the side hole 45 can be placed in the vicinity of the bifurcation 3a, and a fluid such as an anticancer agent can be caused to flow smoothly and effectively through the branch tube 3.

In the embodiment, as shown in FIG. 6B, furthermore, the weakened portion 28 is formed in the whole circumference of the inner tube 20. When the balloon 40 is inflated by the supply of a fluid into the inflation lumen 31, and the weakened portion 28 is pressed, therefore, the pressing force acts on the the whole circumference of the weakened portion 28, and the main lumen 21 of the inner tube 20 can be closed more smoothly.

REFERENCE SIGNS LIST

10 balloon catheter
20 inner tube
21 main lumen
22 inner layer
23 reinforcing member
25 outer layer
28 weakened portion
30 outer tube
31 inflation lumen
40 balloon
45 side hole
50 hub

The invention claimed is:

1. A balloon catheter which has an inflatable balloon in a tip end portion, the balloon catheter including:
   an inner tube which has a main lumen thereinside; and
   an outer tube which is placed on an outer circumference of the inner tube, and which forms an inflation lumen with the inner tube to flow a fluid for inflating the balloon therethough,
   wherein a base end side of the balloon is fixed to the outer tube, whereas a tip end side of the balloon is fixed to the inner tube or the outer tube,
   wherein a part of the inner tube is coupled to the outer tube at a side of a base end with respect to the balloon, and a side hole is formed in the coupling portion to cause the main lumen to be opened to an exterior,
   wherein a weakened portion which is lower in rigidity than another portion of the inner tube is disposed on the inner tube at a side of a tip end with respect to the side hole,
   wherein the weakened portion is configured such that, when the balloon, is inflated by the fluid supplied to the inflation lumen, the weakened portion is pressed by a pressure of the fluid to thereby close the main lumen of the inner tube,
   wherein the weakened portion of the inner tube includes:
      an inner layer which is capable of closing the main lumen by being pressed by the fluid supplied to the inflation lumen; and
      a reinforcing member which is placed on the outer circumference of the inner layer, and which is configured to allow the fluid to pass therethrough, and
   wherein the reinforcing member has a gap which allows the fluid to pass therethrough, is placed on the outer circumference of the inner layer without being fixed thereto, and is configured to be separated from the outer circumference of the inner layer when a diameter of the inner layer is reduced.

2. The balloon catheter of claim 1,
   wherein the weakened portion is configured by forming a part of the inner tube to be thinner than another part.

3. The balloon catheter of claim 1,
   wherein a base end side of the weakened portion is placed on a side of the tip end of the inner tube with respect to a place where the base end side of the balloon is fixed to the outer tube.

4. The balloon catheter of claim 1,
   wherein the weakened portion is formed in a whole circumference of the inner tube.

5. A balloon catheter which has an inflatable balloon in a tip end portion, the balloon catheter including:
   an inner tube which has a main lumen thereinside: and
   an outer tube which is placed on an outer circumference of the inner tube, and which forms an inflation lumen with the inner tube to flow a fluid for inflating the balloon therethrough,
   wherein a base end side of the balloon is fixed to the outer tube, whereas a tip end side of the balloon is fixed to the inner tube or the outer tuber,
   wherein a part of the inner tube is coupled to the outer tube at a side of base end with respect to the balloon, and a side hole formed in the coupling portion to cause the main lumen to be opened to an exterior,
   wherein a weakened portion which is lower in rigidity than another portion of the inner tube is disposed on the inner tube at a side of a tip end with respect to the side hole,
   wherein the weakened portion is configured such that, when the balloon is inflated by the fluid supplied to the inflation lumen, the weakened portion is pressed by a pressure of the fluid to thereby close the main lumen of the inner tube,
   wherein the weakened portion of the inner tube includes:
      an inner layer which is capable of closing the main lumen by being pressed by the fluid supplied to the inflation lumen: and
      a reinforcing member which is placed on the outer circumference of the inner layer, and which is configured to allow the fluid to pass therethrough,
   wherein the inner tube includes:
      the inner layer;
      the reinforcing member; and
      an outer layer which is placed on the outer circumference of the reinforcing member, and which clamps the reinforcing member with the inner layer, and
   wherein, in the weakened portion, a part of the outer layer is peeled off to thereby expose the reinforcing member.

6. The balloon catheter of claim 5,
   wherein the weakened portion is configured by forming a part of the inner tube to be thinner than another part.

7. The balloon catheter of claim 5,
wherein a base end side of the weakened portion is placed on a side of the tip end of the inner tube with respect to a place where the base end side of the balloon is fixed to the outer tube.

8. The balloon catheter of claim 5,
wherein the weakened portion is formed in a whole circumference of the inner tube.

* * * * *